US00PP27132P2

(12) United States Plant Patent
van Opstal

(10) Patent No.: US PP27,132 P2
(45) Date of Patent: Sep. 6, 2016

(54) ***LEUCOTHOE* PLANT NAMED 'OPSTAL 50'**

(50) Latin Name: *Leucothoe keiskei*
Varietal Denomination: Opstal 50

(71) Applicant: Ron van Opstal, Zundert (NL)

(72) Inventor: Ron van Opstal, Zundert (NL)

( * ) Notice: Subject to any disclaimer, the term of this patent is extended or adjusted under 35 U.S.C. 154(b) by 312 days.

(21) Appl. No.: 13/999,880

(22) Filed: Apr. 1, 2014

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

(56) References Cited

PUBLICATIONS http://www.newplantsandflowers.com/burning-leucothoe/; Aug. 19, 2013; 2 pages.*

* cited by examiner

*Primary Examiner* — Kent L Bell
(74) *Attorney, Agent, or Firm* — Penny J. Aguirre

(57) ABSTRACT

A new cultivar of *Leucothoe*, 'Opstal 50', that is characterized by its compact, upright, shrubby plant habit with short internodes, its fine, narrow leaves, and its immature shoots (stems, leaves, and petioles) that are red in color that mature to a green color in summer and turn purple in fall through winter.

2 Drawing Sheets

Botanical classification: *Leucothoe keiskei*.
Variety denomination: 'Opstal 50'.

BACKGROUND OF THE INVENTION

The present invention relates to a new and distinct cultivar of *Leucothoe keiskei*. The new *Leucothoe* will hereafter by its cultivar name, 'Opstal 50'. 'Opstal 50' is a new cultivar of evergreen shrub grown for use as an ornamental landscape plant.

The new cultivar was discovered by the Inventor in May of 2008 as a naturally occurring branch mutation of *Leucothoe keiskei* 'Royal Ruby' (Not Patented) that was growing in a container in Zundert, The Netherlands.

Asexual propagation of the new cultivar was first accomplished by the Inventor using stem cuttings in January of 2009 in Zundert, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Opstal 50' as a unique cultivar of *Leucothoe*.

1. 'Opstal 50' exhibits a broad spreading, upright, shrubby plant habit with short internodes.
2. 'Opstal 50' exhibits fine, narrow leaves.
3. 'Opstal 50' exhibits immature shoots (stems, leaves, and petioles) that are red in color that mature to a green color in summer and turn purple in fall through winter.

'Royal Ruby', the parent of 'Opstal 50', is similar to 'Opstal 50' in plant habit and in having red colored new growth. 'Royal Ruby' differs from 'Opstal 50' in being taller in height and in having leaves that are longer in length and broader in width. 'Opstal 50' can be compared to the *Leucothoe* cultivar 'Curly Red' (U.S. Plant Pat. No. 17,666). 'Curly Red' is similar to 'Opstal 50' in having new growth that is red in color and in having mature growth that is green in color. 'Curly Red' differs from 'Opstal 50' in having curled foliage and in having leaves that are purple in color during the summer.

BRIEF DESCRIPTION OF THE DRAWINGS

The accompanying colored photographs illustrate the overall appearance and distinct characteristics of three year-old plants of the new *Leucothoe* as grown outdoors in 23-cm containers in Zundert, The Netherlands.

The photograph in FIG. 1 provides a side view of the overall plant habit of 'Opstal 50'.

Figure 1:
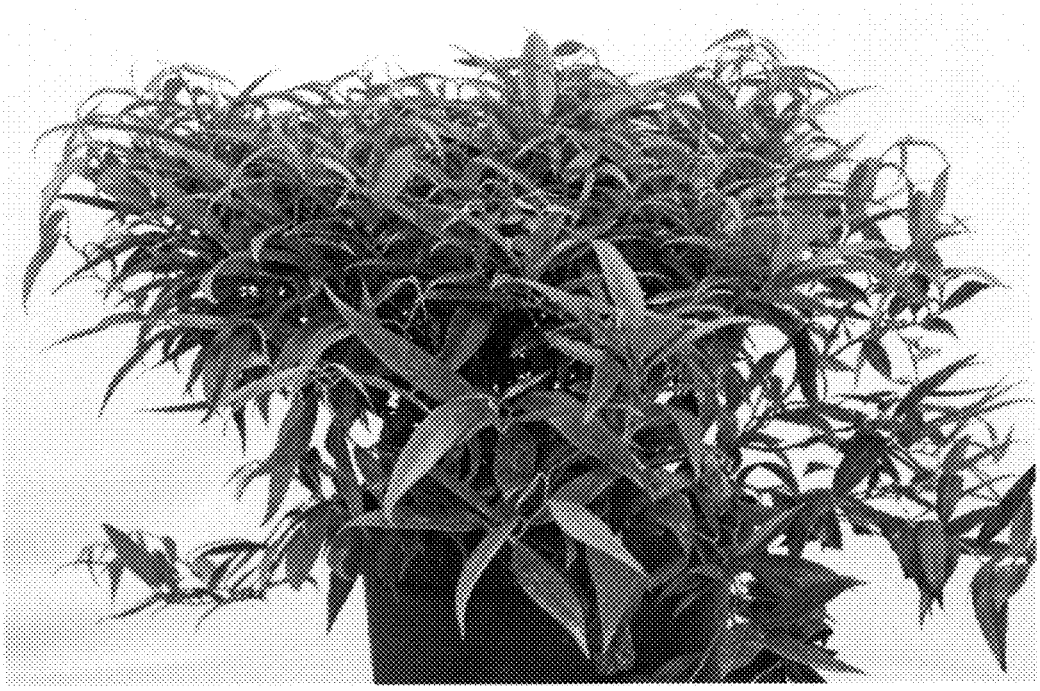
Figure 2:
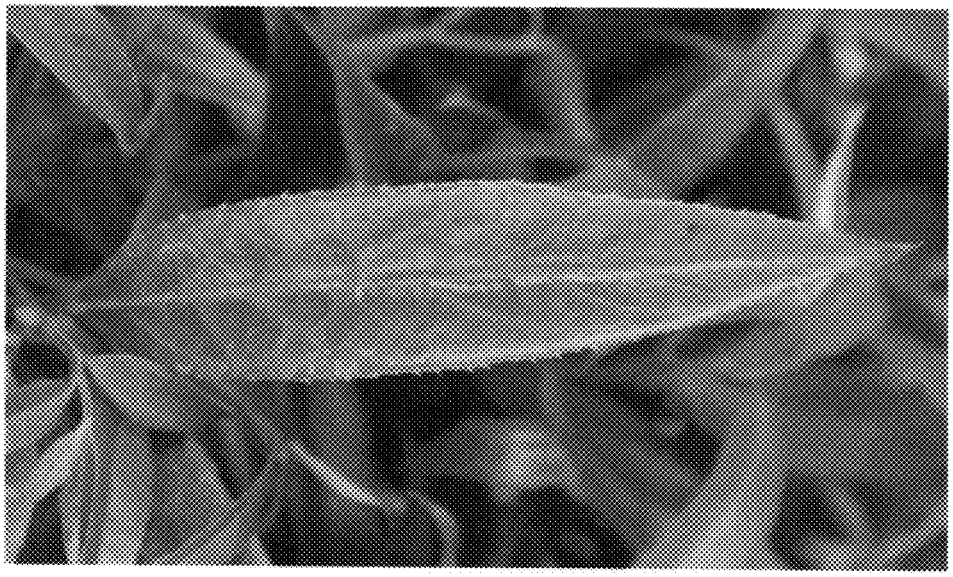

The photograph in FIG. 2 provides a close-up view of a mature leaf of 'Opstal 50'.

Figure 3:
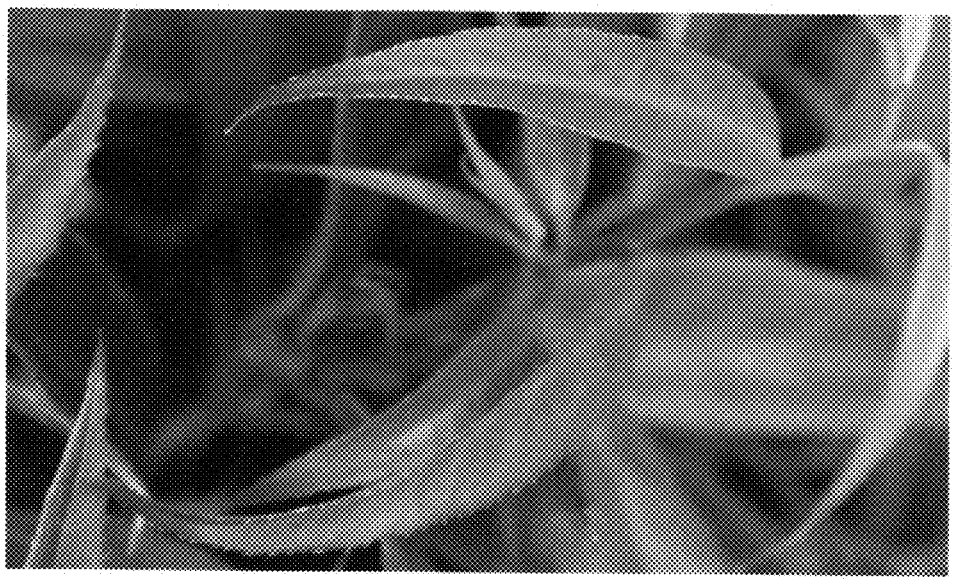

The photograph in FIG. 3 provides a close-up view of the immature foliage of 'Opstal 50'.

The colors in the photograph are as close as possible with the digital photography techniques available and the color values cited in the detailed botanical description most accurately describe the colors of the new *Leucothoe*.

DETAILED BOTANICAL DESCRIPTION

The following is a detailed description of three year-old plants of the new cultivar as grown outdoors in 23-cm containers in Zundert, The Netherlands. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General description:

*Plant type.*—Evergreen perennial shrub.

*Plant habit.*—Compact, upright, shrubby.

*Plant shape.*—Flattened globular.

*Plant size.*—Reaches about 26.7 cm in height and 59.5 cm in spread.

*Cold hardiness.*—At least in U.S.D.A. Zones 5.

*Environmental stress.*—High durability of foliage to wind and rain.

*Plant vigor.*—Moderate.

*Diseases and pests.*—No more susceptibility or resistance to pests and diseases than has been observed.

*Root description.*—Fibrous and fine.

*Propagation*—Stem cuttings.

*Growth rate.*—Moderate.

Stem description:

*Shape.*—Rounded.

*Stem color.*—Young branches; 183B, mature branches; 143B.

*Stem size.*—An average of 18.5 cm in length and 2 mm in diameter.

*Stem surface.*—Smooth and glossy.

*Stem aspect.*—Held at an average angle 60°.

*Branching.*—Very freely branched with basal branching, an average of 61 lateral branches.

*Internode length.*—An average of 1.2 cm.

*Stem strength.*—Very strong.

Foliage description:

*Leaf shape.*—Narrow ovate to lanceolate.

*Leaf division.*—Simple.

*Leaf base.*—Rounded to short attenuate.

*Leaf apex.*—Narrow and long apiculate to narrow acuminate, slightly curled sideways and slightly pointed downward.

*Leaf fragrance.*—None.

*Leaf venation.*—Pinnate, 144C in color on upper surface, 145A in color on lower surface.

*Leaf margins.*—Finely serrate.

*Leaf arrangement.*—Alternate.

*Leaf attachment.*—Petiolate.

*Leaf surface.*—Upper surface; smooth and very glossy, lower surface; slightly glossy.

*Leaf size.*—An average of 7.2 cm in length and 1.5 cm in width.

*Leaf internode length.*—Short, an average of 1 cm.

*Leaf quantity.*—An average of 21 per lateral stem.

*Leaf color.*—New growth upper surface; 175A, new growth lower surface; 177B tinged with 199B, mature growth upper surface; a color between 139A and 147A, but darker, mature growth lower surface; 147B, fall and winter color upper and lower surfaces; a blend of N77A, N77B and 147A.

*Petioles.*—About 6 mm in length and 1.2 mm in width, 144B to 144C in color, glossy and smooth surface.

Inflorescence description: Flowers have not been observed to form and are typically insignificant for the species.

It is claimed:

1. A new and distinct cultivar of *Leucothoe* plant named 'Opstal 50' as herein illustrated and described.

* * * * *